(12) United States Patent
Harada et al.

(10) Patent No.: US 9,493,353 B2
(45) Date of Patent: Nov. 15, 2016

(54) PROCESS FOR PRODUCING PYROPHOSPHATE

(71) Applicant: ADEKA CORPORATION, Tokyo (JP)

(72) Inventors: Genta Harada, Saitama (JP); Yutaka Yonezawa, Saitama (JP); Michio Nakamura, Saitama (JP); Yuri Okamoto, Saitama (JP); Kohei Omori, Saitama (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 14/652,797

(22) PCT Filed: Feb. 14, 2014

(86) PCT No.: PCT/JP2014/053459
§ 371 (c)(1),
(2) Date: Jun. 17, 2015

(87) PCT Pub. No.: WO2014/132814
PCT Pub. Date: Sep. 4, 2014

(65) Prior Publication Data
US 2015/0353513 A1  Dec. 10, 2015

(30) Foreign Application Priority Data
Mar. 1, 2013  (JP) ................ 2013-040951

(51) Int. Cl.
| C07D 251/14 | (2006.01) |
| C07D 251/42 | (2006.01) |
| C07D 251/48 | (2006.01) |
| C07D 251/54 | (2006.01) |
| C07F 9/6521 | (2006.01) |
| C01B 25/42 | (2006.01) |
| C07D 295/02 | (2006.01) |
| C07F 9/6509 | (2006.01) |

(52) U.S. Cl.
CPC ............ *C01B 25/42* (2013.01); *C07D 251/54* (2013.01); *C07D 295/02* (2013.01); *C07F 9/6509* (2013.01)

(58) Field of Classification Search
CPC  C07D 251/14; C07D 251/42; C07D 251/48; C07D 251/54; C07D 295/02; C07F 9/6521; C07F 9/6509; C01B 25/42

USPC ............ 544/200, 214, 195, 204, 337
See application file for complete search history.

(56) References Cited

U.S. PATENT DOCUMENTS

| 3,635,970 A | 1/1972 | Fessler et al. |
| 3,920,796 A | 11/1975 | Sheridan |
| 4,950,757 A | 8/1990 | Tomko et al. |
| 6,268,494 B1 | 7/2001 | Kasowski |
| 7,449,577 B2 | 11/2008 | Kimura et al. |
| 8,314,167 B2 | 11/2012 | Kaneda et al. |
| 9,315,473 B2 * | 4/2016 | Kamimoto ............. C01B 25/42 |
| 2013/0294994 A1 | 11/2013 | Kamimoto et al. |

FOREIGN PATENT DOCUMENTS

| CN | 101121506 | 2/2008 |
| EP | 1674459 | 6/2006 |
| EP | 2295500 | 3/2011 |
| JP | 40-28594 | 12/1965 |
| JP | 49-25675 | 7/1974 |
| JP | 2001-026597 | 1/2001 |
| JP | 2009-001435 | 1/2009 |
| WO | WO 2012/032728 | 3/2012 |

OTHER PUBLICATIONS

Ikutaro Tayama et al., Rinsan'en no Kagaku to Riyo, Kabushiki Kaisha Kagaku Kogyosha, Mar. 1, 1969, p. 141.
International Search Report, PCT/JP2014/053459, May 13, 2014.
Extended European Search Reported—EP 14 75 7173—Jul. 4, 2016.
Chinese Search Report—2014800033751—Aug. 26, 2016.

\* cited by examiner

*Primary Examiner* — Venkataraman Balasubramanian
(74) *Attorney, Agent, or Firm* — Young & Thompson

(57) ABSTRACT

A process for producing a pyrophosphate, particularly melamine pyrophosphate useful as a flame retardant, efficiently in high yield is provided. The process includes firing an orthophosphate, preferably melamine orthophosphate, in the presence of a silicone oil, preferably methylphenyl silicone oil preferably at 120° to 350° C. Examples of useful firing equipment include a hot air dryer, a kneader, a Henschel mixture, a fluidized bed dryer, a rotary kiln, a paddle dryer, an extruder, a vibrating dryer, a far-infrared conveyor furnace, and a microwave firing furnace.

16 Claims, No Drawings

PROCESS FOR PRODUCING PYROPHOSPHATE

TECHNICAL FIELD

This invention relates to a process for producing a pyrophosphate, particularly melamine pyrophosphate useful as a flame retardant.

BACKGROUND ART

A pyrophosphate, particularly melamine pyrophosphate is a compound obtained by bonding between pyrophosphoric acid, which is a polyphosphoric acid, and melamine and is useful as a flame retardant added to paint, synthetic resins, and the like. Various processes for producing melamine pyrophosphate have been so far proposed.

For example, Patent Document 1 below discloses a process comprising mixing melamine and hydrochloric acid in an aqueous solution to make melamine hydrochloride and adding thereto sodium pyrophosphate to precipitate melamine pyrophosphate. However, this process uses an expensive pyrophosphate as a raw material and involves a washing step and a filtration step to remove the halogen and therefore has the problem of high production cost.

Patent Document 2 below teaches preparing melamine pyrophosphate by causing pyrophosphoric acid and melamine to react with each other at 0° to 60° C. in an aqueous solution. This process, too, has the problem of high production cost on account of the use of expensive pyrophosphoric acid and the involvement of a filtration step.

Production of melamine pyrophosphate or melamine polyphosphate by firing melamine orthophosphate to induce dehydration condensation in a solid phase is known as disclosed in Patent Documents 3, 4, and 5 below.

However, when a pyrophosphate such as melamine pyrophosphate is produced by firing melamine orthophosphate in a solid phase to cause dehydration condensation, an unreacted material or a product can adhere to the inner wall of firing equipment or the stirring mechanism such as a stirring blade. This is because of the influences of by-produced water and viscous overreaction products, such as a triphosphate and higher polyphosphates. These substances form a persistent deposit on the inner wall of the firing equipment, the stirring blade, and the like, which hinders uniform heating and firing, and the adhesion loss leads to reduction in yield.

CITATION LIST

Patent Document

Patent Document 1: JP 49-25675B
Patent Document 2: U.S. Pat. No. 4,950,757
Patent Document 3: JP 40-28594B
Patent Document 4: JP 2001-26597A
Patent Document 5: US 2013/0294994

SUMMARY OF THE INVENTION

Problem to be Solved by the Invention

An object of the invention is to provide a process for producing a pyrophosphate efficiently in high yield.

Means for Solving the Problem

As a result of extensive investigations, the inventors have found that the above object is accomplished by firing an orthophosphate in the presence of silicone oil and thus reached the invention.

The invention provides a process for producing a pyrophosphate comprising firing an orthophosphate in the presence of silicone oil.

The invention provides a preferred embodiment of the process, in which the orthophosphate is melamine orthophosphate.

The invention provides another preferred embodiment of the process, in which the silicone oil is methylphenyl silicone oil.

The invention provides still another preferred embodiment of the process, in which the firing temperature is in the range of from 120° to 350° C.

Effect of the Invention

According to the process of the invention, a pyrophosphate, particularly melamine pyrophosphate is provided efficiently in high yield.

BEST MODE FOR CARRYING OUT THE INVENTION

The production process of the invention will be described in detail.

Examples of the pyrophosphate that can be prepared by the process of the invention include ammonium pyrophosphate, melamine pyrophosphate, acetoguanamine pyrophosphate, benzoguanamine pyrophosphate, acrylguanamine pyrophosphate, 2,4-diamino-6-nonyl-1,3,5-triazine pyrophosphate, 2,4-diamino-6-hydroxy-1,3,5-triazine pyrophosphate, 2-amino-4,6-dihydroxy-1,3,5-triazine pyrophosphate, 2,4-diamino-6-methoxy-1,3,5-triazine pyrophosphate, 2,4-diamino-6-ethoxy-1,3,5-triazine pyrophosphate, 2,4-diamino-6-propoxy-1,3,5-triazine pyrophosphate, 2,4-diamino-6-isopropoxy-1,3,5-triazine pyrophosphate, 2,4-diamino-6-mercapto-1,3,5-triazine pyrophosphate, and 2-amino-4,6-dimercapto-1,3,5-triazine pyrophosphate Further included are N,N,N',N'-tetramethyldiaminomethane pyrophosphate, ethylenediamine pyrophosphate, N,N'-dimethylethylenediamine pyrophosphate, N,N'-diethylethylenediamine pyrophosphate, N,N-dimethylethylenediamine pyrophosphate, N,N-diethylethylenediamihne pyrophosphate, N,N,N',N'-tetramethylethylenediamine pyrophosphate, 1,2-propanediamine pyrophosphate, 1,3-propanediamine pyrophosphate, tetramethylenediamine pyrophosphate, pentametylenediamine pyrophosphate, hexamethylenediamine pyrophosphate, 1,7-diaminoheptane pyrophosphate, 1,8-diaminooctane pyrophosphate, 1,9-diaminononane pyrophosphate, 1,10-diaminodecane pyrophosphate, piperazine pyrophosphate, trans-2,5-dimethylpiperazine pyrophosphate, 1,4-bis(2-aminoethyl)piperazine pyrophosphate, and 1,4-bis(3-aminopropyl)piperazine pyrophosphate.

Particularly preferred of them is melamine pyrophosphate in view of achievable high production efficiency and yield.

Examples of the orthophosphate that can be used as a starting material of the pyrophosphate include those corresponding to the pyrophosphates recited above.

The orthophosphate may be a normal salt, an acid salt, or a mixture thereof. The orthophosphate may comprise the base in excess.

A particularly preferred embodiment of the invention is a process for producing melamine pyrophosphate starting with melamine orthophosphate in terms of high yield and high efficiency. The starting melamine orthophosphate is preferably a compound prepared by bonding 1 mole of melamine to 1 mole of orthophosphoric acid.

According to the process of the invention, an orthophosphate is fired to undergo dehydration condensation to give a pyrophosphate.

The firing is preferably carried out in a solid phase. The firing is possible even in the presence of water. The firing is possible even in an aqueous slurry.

The firing temperature is usually 120° to 350° C. From the standpoint of the purity of the resulting pyrophosphate and production efficiency, the firing temperature is preferably 150° to 300° C., more preferably 160° to 280° C. At temperatures lower than 120° C., the progress of dehydration condensation is sometimes insufficient. At temperatures higher than 350° C., excessive dehydration condensation can occur, resulting in the formation of a triphosphate or a higher polyphosphate.

The firing time depends on the temperature condition. The firing is carried out appropriately until the dehydration condensation reaction from an orthophosphate to a pyrophosphate completes.

The orthophosphate as a starting material may be ground or pulverized before being fired. Examples of useful grinders or pulverizers include a ball mill, a rod mill, a hammer mill, an attrition mill, a micron mill, a colloid mill, a jet mill, Single Track Jet Mill, a counter jet mill, a pin disk mill, Jet-O-Mizer and Inomizer.

Examples of the silicone oil for use in the invention include dimethyl silicone oil (polysiloxane having a methyl group at all possible locations), methylphenyl silicone oil (polysiloxane having a phenyl group at part of the side chains), methylhydrogen silicone oil (polysiloxane having hydrogen at part of the side chains), and copolymers thereof. Modified silicone oils derived from these silicone oils by introducing an organic group to part of their side chains and/or terminals are also useful, including amino-modified, epoxy-modified, alicyclic epoxy-modified, carboxyl-modified, carbinol-modified, mercapto-modified, polyether-modified, long-chain alkyl-modified, fluoroalkyl-modified, higher fatty acid ester-modified, higher fatty acid amide-modified, silanol-modified, diol-modified, phenol-modified, and/or aralkyl-modified.

Preferred of them is methylphenyl silicone oil in terms of prevention of adhesion of deposits to the inner wall of the firing equipment or the stirring mechanism, such as a stirring blade.

Specifically, examples of dimethyl silicone oil are KF-96, KF-965, and KF-968 (all from Shin-Etsu Chemical Co., Ltd.). Examples of methylhydrogen silicone oil or silicone oil having a methylhydrogen polysiloxane structure include KF-99 and KF-9901 (both from Shin-Etsu Chemical), HMS-151, HMS-071, HMS-301, and DMS-H21 (all from Gelest, Inc.). Examples of methylphenyl silicone oil are KF-50, KF-53, KF-54, and KF-56 (all from Shin-Etsu Chemical). Examples of epoxy-modified silicone oil include X-22-343, X-22-2000, KF-101, KF-102, and KF-1001 (all from Shin-Etsu Chemical). Examples of carboxyl-modified silicone oil include X-22-3701E (from Shin-Etsu Chemical). Examples of carbinol-modified silicone oil are X-22-4039 and X-22-4015 (both from Shin-Etsu Chemical). Amine-modified silicone oil is exemplified by KF-393 (from Shin-Etsu Chemical).

The amount of the silicone oil to be used is preferably 0.01 to 2 parts, more preferably 0.05 to 0.5 parts, even more preferably 0.1 to 0.3 parts, by mass per 100 parts by mass of the orthophosphate to be fired. At amounts less than 0.01 parts, a deposit can increase. Using more than 2 parts of silicone oil can affect the physical properties of the resulting product or make the system too fluid. Excessive fluidity of the system can hinder sufficient progress of the firing reaction in a continuous firing process.

To carry out the firing, heat kneaders, hot air dryers, firing furnaces/kilns, and so on may be used. Examples of them include an extruder, a Henschel mixer, a flash mixer, a paddle mixer, a Banbury mixer, a ribbon mixer, a crush mixer, an SC processor, a Plastomill, a KRC kneader, a vacuum kneader, a pressure kneader, a firing furnace, a batch furnace, a pusher furnace, a mesh belt furnace, a fluidized-bed firing furnace, a double-shaft continuous firing furnace, a far-infrared heating furnace, a far-infrared conveyer furnace, a microwave firing furnace, a crucible furnace, a hot air dryer, a fluidized bed dryer, a vibrating dryer, a vibrating fluidized bed dryer, a stirring dryer, a pneumatic dryer, a through-air dryer, a tray dryer, a Drymeister, a drum dryer, an air dryer, a microwave dryer, a spray dryer, a disk dryer, a conical dryer, a paddle dryer, a hopper dryer, a rotary dryer, a rotary kiln, a roller hearth kiln, a tunnel kiln and a shuttle kiln.

According to the process of the invention, formation of deposits onto the inner wall of the firing equipment and the stirring mechanism, such as a stirring blade, is prevented to allow for efficient and high yield production of a desired product.

The pyrophosphate obtained by the process of the invention is suited for use as a flame retardant for synthetic resins.

EXAMPLES

The invention will now be illustrated in greater detail with reference to Examples and Comparative Examples, but it should be understood that the invention is not deemed to be limited thereto.

Example 1

Production of Melamine Pyrophosphate by Use of Hot Air Dryer

A stainless steel vat containing a mixture of 100 g of melamine orthophosphate and 0.2 g of methylphenyl silicone oil (KF-50 from Shin-Etsu Chemical Co., Ltd.) was placed in a hot air dryer (LC-234 from ESPEC Corp.), heated with occasional stirring with a stainless steel blade, and fired at 200° to 260° C. for 3 hours to give 94 g of melamine pyrophosphate as white powder in a yield of 98% relative to the theoretical yield (96 g). After the firing, substantially no deposits were observed on the stirring blade and the vat.

Example 2

Production of Melamine Pyrophosphate by Use of Kneader

A thousand grams of melamine orthophosphate and 2 g of methylphenyl silicone oil (KF-50 from Shin-Etsu Chemical) were put in a oil-jacketed kneader, stirred while heating, and fired at 200° to 250° C. for 3 hours to give 920 g of melamine pyrophosphate as white powder in a yield of 96% relative to the theoretical yield (960 g). After the firing, substantially no deposits were observed on the blades and inner wall of the kneader.

Example 3

Production of Melamine Pyrophosphate by Use of Henschel Mixer

Thirty kilograms of melamine orthophosphate and 60 g of methylphenyl silicone oil (KF-50 from Shin-Etsu Chemical) were put in a Henschel mixer (FM150J/T from Mitsui Mining & Smelting Co., Ltd.) jacketed with a heating medium, stirred while heating, and fired at 200° to 250° C. for 3 hours to give 28 kg of melamine pyrophosphate as white powder in a yield of 97% relative to the theoretical yield (28.8 Kg). After the firing, substantially no deposits were observed on the blades and the inner wall of the Henschel mixer.

Example 4

Production of Melamine Pyrophosphate by Use of Fluidized Bed Dryer

A total of 250 kg of a mixture of 100 parts by mass of melamine orthophosphate and 0.2 parts by mass of methylphenyl silicone oil (KF-50 from Sin-Etsu Chemical) was continuously fed to a fluidized bed dryer (from Okawara MFG Co., Ltd.) at a rate of 5 kg per hour and fired at 230° to 260° C. Fifty hour continuous operation produced 216 kg of melamine pyrophosphate as white powder in a yield of 90% relative to the theoretical yield (240 kg). After the continuous operation, substantially no deposits were observed on the inner wall of the fluidized bed dryer.

Example 5

Production of Melamine Pyrophosphate by Use of Rotary Kiln

A total of 250 kg of a mixture of 100 parts by mass of melamine orthophosphate and 0.2 parts by mass of methylphenyl silicone oil (KF-50 from Sin-Etsu Chemical) was continuously fed to a rotary kiln (from Kurimoto, Ltd.) at a rate of 5 kg per hour and fired at 200° to 260° C. Fifty hour continuous operation produced 216 kg of melamine pyrophosphate as white powder in a yield of 90% relative to the theoretical yield (240 kg). After the continuous operation, substantially no deposits were observed on the inner wall of the rotary kiln.

Example 6

Production of Melamine Pyrophosphate by Use of Paddle Dryer

A total of 210 kg of a mixture of 100 parts by mass of melamine orthophosphate and 0.2 parts by mass of methylphenyl silicone oil (KF-50 from Sin-Etsu Chemical) was continuously fed to a paddle dryer (NPD-3W-G from Nara Machinery Co., Ltd.) at a rate of 3 kg per hour and fired at 200° to 260° C. Seventy hour continuous operation produced 180 kg of melamine pyrophosphate as white powder in a yield of 90% relative to the theoretical yield (200 kg). After the continuous operation, substantially no deposits were observed on the paddles and the inner wall of the paddle dryer.

Example 7

Production of Melamine Pyrophosphate by Use of Extruder

A total of 250 kg of a mixture of 100 parts by mass of melamine orthophosphate and 0.2 parts by mass of methylphenyl silicone oil (KF-50 from Sin-Etsu Chemical) was continuously fed to an extruder (TEX44αII-52.5BW from The Japan Steel Works, Ltd.) at a rate of 5 kg per hour and fired at 120° to 280° C. Fifty hour continuous operation produced 218 kg of melamine pyrophosphate as white powder in a yield of 91% relative to the theoretical yield (240 kg). After the continuous operation, substantially no deposits were observed on the screw and the inner wall of the cylinder of the extruder.

Example 8

Production of Melamine Pyrophosphate by Use of Vibrating Dryer

Twenty-two kilograms of melamine orthophosphate and 40 g of methylphenyl silicone oil (KF-50 from Shin-Etsu Chemical) were put in a vibrating dryer (from Chuo Kakoki Co., Ltd.), stirred while heating, and fired at 200° to 260° C. for 3 hours to give 20.5 kg of melamine pyrophosphate as white powder in a yield of 98% relative to the theoretical yield (21 Kg). After the firing, substantially no deposits were observed on the inner wall of the vibrating dryer.

Example 9

Production of Melamine Pyrophosphate by Use of Far-Infrared Conveyor Furnace

A total of 150 kg of a mixture of 100 parts by mass of melamine orthophosphate and 0.2 parts by mass of methylphenyl silicone oil (KF-50 from Sin-Etsu Chemical) was continuously fed to a far-infrared conveyor furnace (LF-AN2-154 from Noritake Co., Inc.) at a rate of 3 kg per hour and fired at 220° to 230° C. Fifty hour continuous operation produced 130 kg of melamine pyrophosphate as white powder in a yield of 90% relative to the theoretical yield (144 kg). After the continuous operation, substantially no deposits were observed on the conveyor of the far-infrared conveyor furnace.

Example 10

Production of Melamine Pyrophosphate by Use of Microwave Firing Furnace

A ceramic container containing a mixture of 100 g of melamine orthophosphate and 0.2 g of methylphenyl silicone oil (KF-50 from Shin-Etsu Chemical) was placed in a microwave firing furnace (from Komatsubara, Ltd.), heated with occasional agitation outside the microwave furnace, and fired at 200° to 280° C. to give 94 of melamine pyrophosphate as white powder in a yield of 98% relative to the theoretical yield (96 g). After the firing, substantially no deposits were observed on the inner wall of the container.

Comparative Example 1

Use of Hot Air Dryer

Firing was carried out in the same manner as in Example 1, except that methylphenyl silicone oil was not used, to give 75 g of melamine pyrophosphate as white powder in a yield of 78% relative to the theoretical yield (96 g). After the firing, a considerable amount of deposits was observed on the stirring blade and the vat.

Comparative Example 2

Use of Kneader

Firing was carried out in the same manner as in Example 2, except for using no methylphenyl silicone oil, to give 768 g of melamine pyrophosphate as white powder in a yield of 80% relative to the theoretical yield (960 g). After the firing, a considerable amount of deposits was observed on the blade and the inner wall of the kneader.

Comparative Example 3

Use of Henschel Mixer

Firing was carried out in the same manner as in Example 3, except for using no methylphenyl silicone oil, to give 23 kg of melamine pyrophosphate as white powder in a yield of 80% relative to the theoretical yield (28.8 kg). After the firing, a considerable amount of deposits was observed on the blade and the inner wall of the Henschel mixer.

Comparative Example 4

Use of Fluidized Bed Dryer

Firing was carried out in the same manner as in Example 4, except for using no methylphenyl silicone oil. The continuous operation was stopped in 30 hours because of the progress of overreaction due to a considerable amount of deposits on the inner wall of the dryer. There was obtained 120 kg of melamine pyrophosphate as white powder in a yield of 83% relative to the theoretical yield (144 kg). After the continuous operation, a considerable amount of deposits was observed on the inner wall of the fluidized bed dryer.

Comparative Example 5

Use of Rotary Kiln

Firing was carried out in the same manner as in Example 5, except for using no methylphenyl silicone oil. The continuous operation was stopped in 25 hours because of the progress of overreaction due to a considerable amount of deposits on the inner wall of the kiln. There was obtained 95 kg of melamine pyrophosphate as white powder in a yield of 85% relative to the theoretical yield (112 kg). After the continuous operation, a considerable amount of deposits was observed on the inner wall of the rotary kiln.

Comparative Example 6

Use of Paddle Dryer

Firing was carried out in the same manner as in Example 6, except for using no methylphenyl silicone oil. The continuous operation was stopped in 35 hours because of the progress of overreaction due to a considerable amount of deposits on the inner wall of the dryer. There was obtained 80 kg of melamine pyrophosphate as white powder in a yield of 80% relative to the theoretical yield (100 kg). After the continuous operation, a considerable amount of deposits was observed on the paddles and the inner wall of the paddle dryer.

Comparative Example 7

Use of Extruder

Firing was carried out in the same manner as in Example 7, except for using no methylphenyl silicone oil. The continuous operation was stopped in 20 hours because of an increase in torque and progress of overreaction. There was obtained 75 kg of melamine pyrophosphate as white powder in a yield of 78% relative to the theoretical yield (96 kg). After the continuous operation, a considerable amount of deposits was observed on the screw and the inner wall of the cylinder of the extruder.

Comparative Example 8

Use of Vibrating Dryer

Firing was carried out in the same manner as in Example 8, except for using no methylphenyl silicone oil, to give 18 kg of melamine pyrophosphate as white powder in a yield of 86% relative to the theoretical yield (21 Kg). After the firing, a considerable amount of deposits was observed on the inner wall of the vibrating dryer.

Comparative Example 9

Use of Far-Infrared Conveyor Furnace

Firing was carried out in the same manner as in Example 9, except for using no methylphenyl silicone oil. The continuous operation was stopped in 30 hours because of the progress of overreaction due to considerable deposits on the inner wall. There was obtained 73 kg of melamine pyrophosphate as white powder in a yield of 85% relative to the theoretical yield (86 kg). After the continuous operation, a considerable amount of deposits were observed on the conveyor of the far-infrared conveyor furnace.

Comparative Example 10

Use of Microwave Firing Oven

Firing was carried out in the same manner as in Example 10, except for using no methylphenyl silicone oil, to give 75 g of melamine pyrophosphate as white powder in a yield of 78% relative to the theoretical yield (96 g). After the continuous operation, a considerable amount of deposits were observed on the inner wall of the container.

The invention claimed is:

1. A process for producing a pyrophosphate comprising firing an orthophosphate in the presence of a silicone oil, the pyrophosphate being selected from the group consisting of ammonium pyrophosphate, melamine pyrophosphate, acetoguanamine pyrophosphate, benzoguanamine pyrophosphate, acrylguanamine pyrophosphate, 2,4-diamino-6-nonyl-1,3,5-triazine pyrophosphate, 2,4-diamino-6-hydroxy-1,3,5-triazine pyrophosphate, 2-amino-4,6- dihydroxy-1,3,5-triazine pyrophosphate, 2,4-diamino-6-methoxy-1,3,5-triazine pyrophosphate, 2,4-diamino-6-ethoxy-1,3,5-triazine pyrophosphate, 2,4-diamino-6-propoxy-1,3,5-triazine pyrophosphate, 2,4-diamino-6-isopropoxy-1,3,5-triazine pyrophosphate, 2,4-diamino-6-mercapto-1,3,5-triazine pyrophosphate, 2-amino-4,6-dimercapto-1,3,5-triazine pyrophosphate, N,N,N',N'-tetramethyldiaminomethane pyrophosphate, ethylenediamine pyrophosphate, N,N'-dimethylethylenediamine pyrophosphate, N,N'-diethylethylenediamine pyrophosphate, N,N-dimethylethylenediamine pyrophosphate, N,N-diethylethylenediamihne pyrophosphate, N,N,N',N'-tetramethylethylenediamine pyrophosphate, 1,2-propanediamine pyrophosphate, 1,3-propanediamine pyrophosphate, tetramethylenediamine pyrophosphate, pentamethylenediamine pyrophosphate, hexamethylenediamine pyrophosphate, 1,7-diaminoheptane pyrophosphate, 1,8-diaminooctane pyrophosphate, 1,9-diaminononane pyrophosphate, 1,10-diaminodecane pyrophosphate, piperazine pyrophosphate, trans-2,5-dimethylpiperazine pyrophosphate, 1,4-bis(2-aminoethyl)piperazine pyrophosphate, and 1,4-bis(3-aminopropyl)piperazine pyrophosphate.

2. The process according to claim 1, wherein the orthophosphate is melamine orthophosphate and the pyrophosphate is melamine pyrophosphate.

3. The process according to claim 1, wherein the silicone oil is methylphenyl silicone oil.

4. The process according to claim 1, wherein the firing is at a temperature of 120° to 350° C.

5. The process according to claim 2, wherein the silicone oil is methylphenyl silicone oil.

6. The process according to claim 2, wherein the firing is at a temperature of 120° to 350° C.

7. The process according to claim 3, wherein the firing is at a temperature of 120° to 350° C.

8. The process according to claim 5, wherein the firing is at a temperature of 120° to 350° C.

9. A process for producing melamine pyrophosphate comprising firing melamine orthophosphate in the presence of a silicone oil.

10. The process according to claim 9, wherein the silicone oil is methylphenyl silicone oil.

11. The process according to claim 9, wherein the firing is at a temperature of 120° to 350° C.

12. The process according to claim 10, wherein the firing is at a temperature of 120° to 350° C.

13. The process according to claim 1, wherein the firing temperature is 150° to 300° C.

14. The process according to claim 1, wherein the firing temperature is 160° to 280° C.

15. The process according to claim 9, wherein the firing temperature is 150° to 300° C.

16. The process according to claim 9, wherein the firing temperature is 160° to 280° C.

\* \* \* \* \*